(12) United States Patent
Boccoleri et al.

(10) Patent No.: US 11,121,583 B2
(45) Date of Patent: Sep. 14, 2021

(54) OPERATING ROOM WIRELESS POWER TRANSFER

(71) Applicant: STRYKER CORPORATION, Kalamazoo, MI (US)

(72) Inventors: Gianni Boccoleri, Lantana, TX (US); Robert Lee York, Lantana, TX (US); Wojciech Kazimierz Timoszyk, Flower Mound, TX (US); Sean Victor Hastings, Flower Mound, TX (US); James K Alexanderson, Coppell, TX (US)

(73) Assignee: Stryker Corporation, Kalamazoo, MI (US)

(*) Notice: Subject to any disclaimer, the term of this patent is extended or adjusted under 35 U.S.C. 154(b) by 21 days.

(21) Appl. No.: 16/254,749

(22) Filed: Jan. 23, 2019

(65) Prior Publication Data

US 2019/0229559 A1    Jul. 25, 2019

Related U.S. Application Data

(60) Provisional application No. 62/620,745, filed on Jan. 23, 2018.

(51) Int. Cl.
*H02J 50/40* (2016.01)
*H02J 50/12* (2016.01)
(Continued)

(52) U.S. Cl.
CPC .......... *H02J 50/40* (2016.02); *A61B 1/00029* (2013.01); *A61B 1/04* (2013.01); *A61B 1/0684* (2013.01); *A61B 1/0692* (2013.01); *A61B 46/20* (2016.02); *A61B 90/30* (2016.02); *A61B 90/98* (2016.02); *A61G 12/004* (2013.01);
(Continued)

(58) Field of Classification Search
CPC .. H02J 50/12; H02J 50/10; H02J 50/20; H02J 50/30; H02J 50/40; H02J 50/60; H02J 50/80; H02J 50/90; A61B 1/04; A61B 1/0684; A61B 1/0692; A61B 1/00029;
(Continued)

(56) References Cited

U.S. PATENT DOCUMENTS 4,052,980 A   10/1977  Grams et al.
4,337,763 A    7/1982  Petrassevich
(Continued)

OTHER PUBLICATIONS

Energous Corporation. (Aug. 12, 2014). "WattUp Demo," located at https://www.youtube.com/watch?v=e0LAzFB0Qh8&feature=youtu.be (3 pages).
(Continued)

*Primary Examiner* — Rexford N Barnie
*Assistant Examiner* — Jagdeep S Dhillon
(74) *Attorney, Agent, or Firm* — Morrison & Foerster LLP (57) ABSTRACT

A surgical room power system including at least one source of power wired to a power source for a surgical room, the at least one source of power being wired to the surgical room; at least one power receiver; and a surgical power consumer wired to the at least one power receiver, the surgical power consumer being configured to assist a surgeon during a surgical procedure on a patient. The at least one source of power wirelessly transfers power to the at least one power receiver for powering the surgical power consumer.

43 Claims, 6 Drawing Sheets

(51) Int. Cl.
*H02J 50/20* (2016.01)
*H02J 50/30* (2016.01)
*A61B 1/00* (2006.01)
*A61B 46/20* (2016.01)
*A61G 13/10* (2006.01)
*A61B 1/06* (2006.01)
*A61B 90/98* (2016.01)
*A61B 1/04* (2006.01)
*A61B 90/30* (2016.01)
*A61G 12/00* (2006.01)

(52) U.S. Cl.
CPC ......... *A61G 12/005* (2013.01); *A61G 12/007* (2013.01); *A61G 12/008* (2013.01); *A61G 13/107* (2013.01); *H02J 50/12* (2016.02); *H02J 50/20* (2016.02); *H02J 50/30* (2016.02); *A61B 2560/0214* (2013.01); *A61G 2203/80* (2013.01); *A61G 2205/60* (2013.01)

(58) Field of Classification Search
CPC . A61B 46/20; A61B 2560/0214; A61B 90/30; A61B 90/98; A51G 12/008
USPC .............. 307/104, 149, 66, 64, 82, 38
See application file for complete search history.

(56) References Cited

U.S. PATENT DOCUMENTS

| | | | |
|---|---|---|---|
| 5,520,611 A | 5/1996 | Rao et al. | |
| 5,914,585 A * | 6/1999 | Grabon | G06F 1/1632 320/125 |
| 6,073,284 A * | 6/2000 | Borders | A61F 7/007 5/600 |
| 6,096,025 A * | 8/2000 | Borders | G16H 40/67 606/1 |
| 6,142,935 A | 11/2000 | Flom et al. | |
| 6,692,489 B1 * | 2/2004 | Heim | A61B 18/12 606/34 |
| 7,306,559 B2 | 12/2007 | Williams | |
| 7,503,894 B2 | 3/2009 | Vankoski et al. | |
| 2003/0066537 A1 * | 4/2003 | Fabian | G01V 15/00 128/899 |
| 2006/0169288 A1 * | 8/2006 | Kleen | A61B 90/00 128/845 |
| 2010/0082368 A1 * | 4/2010 | Gecelter | A61B 90/90 705/3 |
| 2010/0283599 A1 * | 11/2010 | Ma | A61B 34/74 340/539.1 |
| 2011/0286578 A1 * | 11/2011 | Butzine | A61B 6/4405 378/98.5 |
| 2012/0139355 A1 * | 6/2012 | Ganem | H03H 7/40 307/104 |
| 2014/0275973 A1 * | 9/2014 | Schuele | A61B 46/10 600/415 |
| 2015/0055323 A1 * | 2/2015 | Schreiber | F21V 21/30 362/96 |
| 2015/0100066 A1 * | 4/2015 | Kostrzewski | A61B 90/11 606/130 |
| 2015/0148615 A1 * | 5/2015 | Brennan | A61B 50/33 600/249 |
| 2015/0164611 A1 * | 6/2015 | Nemoto | G06F 16/35 707/737 |
| 2016/0045247 A1 * | 2/2016 | Heim | A61B 18/1402 606/45 |
| 2016/0180046 A1 * | 6/2016 | Sezeur | G06F 3/017 700/90 |
| 2016/0271281 A1 * | 9/2016 | Clynne | A61L 2/10 |
| 2017/0143429 A1 * | 5/2017 | Richmond | A61B 34/25 |
| 2017/0236514 A1 * | 8/2017 | Nelson | G10L 15/22 704/257 |
| 2017/0373522 A1 | 12/2017 | Pelosi et al. | |
| 2017/0373537 A1 | 12/2017 | Dayal et al. | |
| 2018/0049825 A1 * | 2/2018 | Kwon | A61B 34/30 |
| 2018/0049839 A1 * | 2/2018 | Seong | B25J 9/1602 |
| 2018/0325621 A1 * | 11/2018 | Srimohanarajah | A61B 90/39 |
| 2018/0353257 A1 * | 12/2018 | Tan | A61B 90/36 |
| 2019/0327394 A1 * | 10/2019 | Ramirez Luna | H04N 5/2252 |

OTHER PUBLICATIONS

Wikipedia. (Dec. 6, 2017). "Resonant inductive coupling," located at https://en.wikipedia.org/wiki/Resonant_inductive_coupling visited on Dec. 13, 2017. (10 pages).

* cited by examiner

OPERATING ROOM WIRELESS POWER TRANSFER

CROSS REFERENCE TO RELATED APPLICATION

This application claims the benefit of U.S. Provisional Application Ser. No. 62/620,745, filed Jan. 23, 2018, the entire contents of which are hereby incorporated herein by reference.

FIELD OF THE INVENTION

The present invention relates to a power transmission, and in particular to wireless power transmission in an operating room.

BACKGROUND OF THE INVENTION

In operating rooms, many surgical devices require power to function. Such powered devices in the operating rooms include power cords that can clutter the room and can make movement over and around such cords precarious. Moreover, devices tied to such power cords can limit movement of people using such devices. If the powered devices use battery power, care must be taken that the batteries supplying power to such devices are sufficiently charged to properly maintain needed power to such devices during a surgical procedure.

It is desired to have an easier way to power devices in an operating room.

SUMMARY OF THE INVENTION

The present invention, according to one aspect, is directed to a surgical room power system including at least one source of power wired to a power source for a surgical room, the at least one source of power being wired to the surgical room; at least one power receiver; and a surgical power consumer wired to the at least one power receiver, the surgical power consumer being configured to assist a surgeon during a surgical procedure on a patient. The at least one source of power wirelessly transfers power to the at least one power receiver for powering the surgical power consumer.

Yet another aspect of the present invention is to provide a method of supplying power to a surgical power consumer in an operating room, the method comprises providing a surgical patient; conducting a surgical procedure on the surgical patient; wiring at least one source of power to a power source for the surgical room; providing at least one power receiver; wiring a surgical power consumer to the at least one power receiver, the surgical power consumer being configured to assist a surgeon during the surgical procedure on the patient; and wirelessly transferring power from the source of power to the power receiver for powering the surgical power consumer.

Yet another aspect of the present invention is to provide a medical room power system comprising a source of power wired to a power source for a medical room, with the source of power being wired to the medical room. The medical room power system further includes a power receiver and a medical power consumer wired to the power receiver, with the medical power consumer being configured to assist a physician during a medical procedure on a patient. The source of power wirelessly transfers power to the power receiver for powering the medical power consumer.

Another aspect of the present invention is to provide a method of supplying power to medical power consumers in a medical room. The method comprises wiring a source of power to a power source for the medical room; providing at least one power receiver; wiring at least one of the medical power consumers to the at least one power receiver, with the medical power consumers being configured to assist a physician during a medical procedure; determining a number of the medical power consumers; ranking the medical power consumers; determining an order for supplying power to the medical power consumers according to the ranking of the medical power consumers; and wirelessly transferring power from the source of power to the at least one power receiver for powering the medical power consumers according to the order.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings and described in the following specification are simply exemplary embodiments of the inventive concepts. Hence, specific dimensions and other physical characteristics relating to the embodiments disclosed herein are not to be considered as limiting.

DETAILED DESCRIPTION

Figure 1:
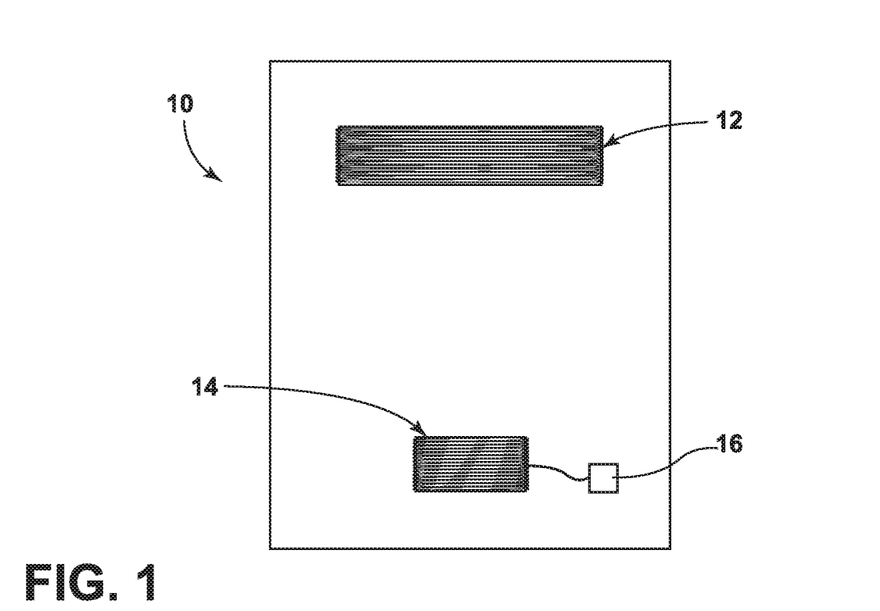
FIG. 1 is a schematic diagram illustrating wireless power transfer from a source to a receiver connected to a power consumer within an operating room of the present invention.

The reference number 10 (FIG. 1) generally designates an operating room of the present invention. The operating room 10 includes a source 12 for transmitting energy wirelessly to a receiver 14 for powering a power consumer 16 wired to the receiver 14. The illustrated power consumer 16 can be any device that can be powered. For example, the power consumer 16 can be a light (e.g., LED) or can be a rechargeable battery. Further examples of power consumers 16 are outlined below. In the present invention, the source 12 is wired to a power source supplied to the operating room 10. In the illustrated example, the wireless power transmission can use resonant inductive coupling as is well known to those skilled in the art. In resonant inductive coupling, the source 12 comprises a primary coil having power passing therethrough to generate a magnetic field and the receiver 14 comprises a secondary coil located in the magnetic field. The secondary coil of the receiver 14 forms an LC circuit and the power of the primary coil of the source 12 is driven at the resonant frequency of the secondary coil of the receiver 14 to transmit power to the receiver 14. Power is transmitted from the receiver 14 to the power consumer 16 to power the power consumer 16.

Figure 2:
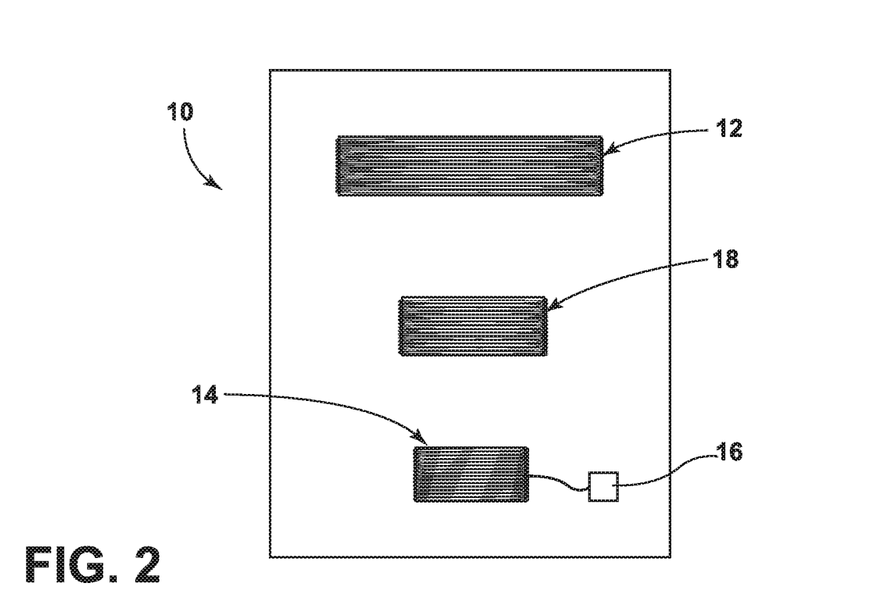
FIG. 2 is a schematic diagram illustrating wireless power transfer from the source to the receiver within the operating room via a booster coil of the present invention.

FIG. 2 illustrates the surgical room 10 with a passive booster coil 18 located between the source 12 and the receiver 14 for extending the distance power can be wirelessly transmitted from the source 12 to the receiver 14. In the illustrated example, the booster coil 18 is magnetically coupled to both the source 12 and the receiver 14 to thereby extend the usable distance between the source 12 and the receiver 14 while continuing to allow the receiver 14 to have power wirelessly transmitted thereto.

Figure 3:
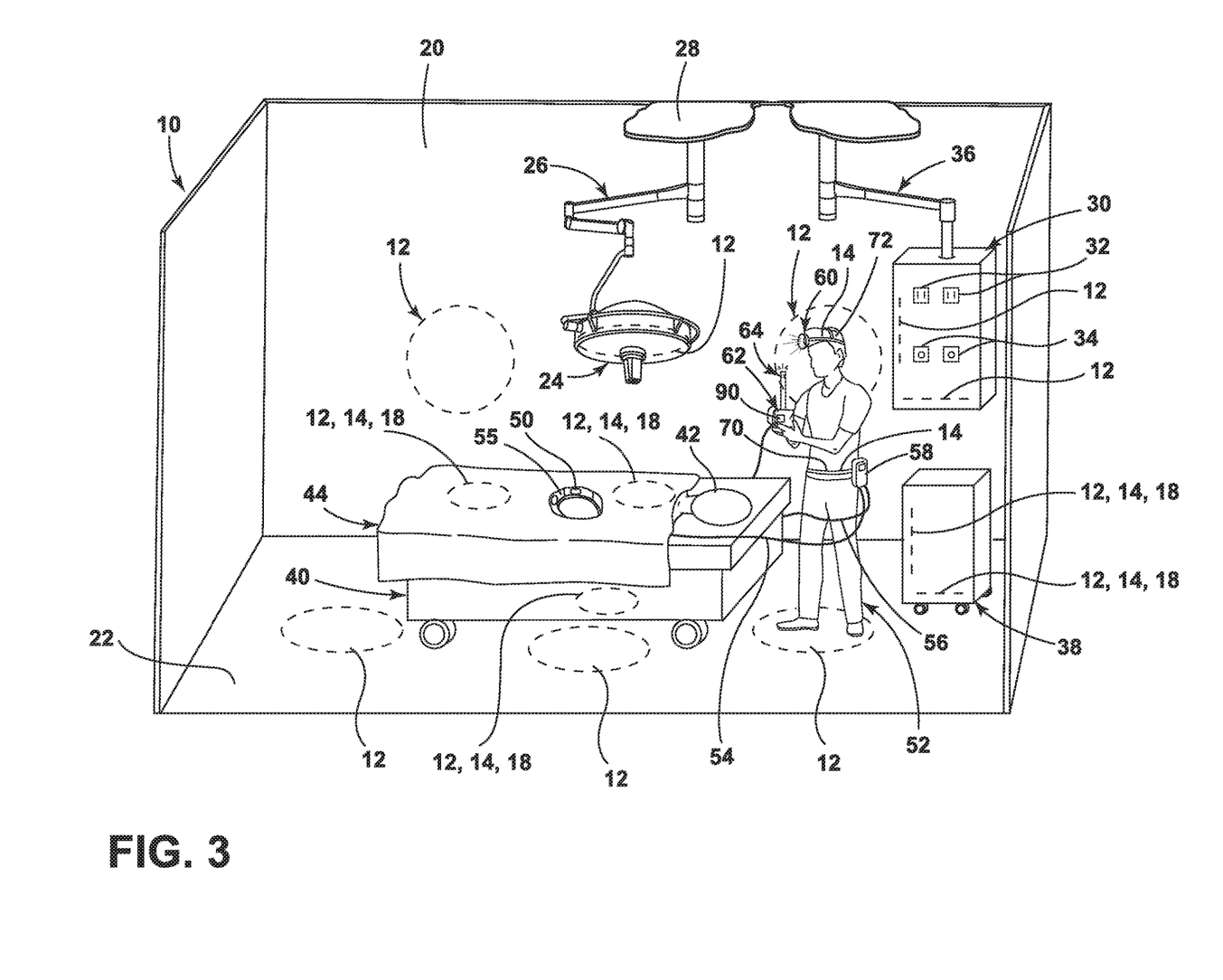
FIG. 3 illustrates a perspective view of an operating room showing a plurality of sources, receivers and power consumers of the present invention.

FIG. 3 illustrates an example of the operating room 10 having a plurality of the sources 12, the receivers 14, the power consumers 16, coils that could either be a source 12 or a booster coil 18, or coils that could either be a source 12, a receiver 14 or a booster coil 18. In the illustrated example, the operating room 10 includes a plurality of sources 12. However, the operating room 10 could have any number of sources 12 including only a single source 12. Likewise, while the operating room 10 includes a plurality of receivers 14 and power consumers 16, the operating room 10 could have any number of receivers 14 and power consumers 16 including only a single receiver 14 or a single power consumer 16. Furthermore, any number of booster coils 18 could be used including a single or even no booster coil 18.

In the illustrated example, the sources 12 could be fixed in the operating room 10 in a fixed location, could be fixed in the operating room 10 in a movable location or could be located in objects that that are able to be moved within and removed from the operating room 10. Examples of sources 12 that would be fixed in the operating room 10 in a fixed location includes sources 12 in walls 20 of the operating room 10 or under the floor 22 of the operating room 10. The fixed location sources 12 could also be located in any device or structure in the operating room 10 that does not move (e.g., fixed cabinets). An example of sources 12 that would be fixed in the operating room 10 in a movable location includes sources 12 in an overhead surgical light 24 at the end of a movable boom 26 connected to a ceiling 28 as shown in FIG. 3 or connected to the wall 20 of the operating room 10 (not shown). Another example of sources 12 that would be fixed in the operating room 10 in a movable location includes sources 12 in a service head 30 including power outlets 32 and gas outlets 34 on a face thereof at the end of a movable boom 36 connected to the ceiling 28 as shown in FIG. 3 or connected to the wall 20 of the operating room 10 (not shown). Further examples are contemplated.

It is contemplated that coils located in the operating room 10 could be used as the source 12, the receivers 14, or the booster coil 18, depending on wired connections and desired uses. A first example of coils that could be the source 12, the receivers 14, or the booster coil 18 includes the sources 12 that can be located in objects that that are able to be moved within and removed from the operating room 10. For example, as illustrated in FIG. 3, the operating room 10 can include a cart 38 having one or more sources 12. The cart 38 could be plugged into a normal outlet in the operating room 10 to thereby supply power to sources 12 within the cart 38. The cart 38 could include a single source 12 or multiple sources 12 to provide a larger field for supplying power to receivers 14. Another object in the operating room 10 that can include the source 12 is a surgical table 40 for supporting a patient 42 in the operating room 10. It is contemplated that the surgical table 40 could be fixed within the operating room 10 to thereby fix the source 12 in the surgical table 40 in position. However, the surgical table 40 could be movable (as illustrated in FIG. 3) to allow the location of the surgical table 40 in the operating room 10 to change or to allow the patient 42 to be moved into and out of the operating room 10. If the surgical table 40 includes one or more sources 12, the surgical table 40 could be plugged into a normal outlet in the operating room 10 to thereby supply power to sources 12 within the surgical table 40. A further example as illustrated in FIG. 3 is a surgical drape 44 positioned over the patient 42. The surgical drape 44 can be configured to be used a single time or can be configured to be sterilizable for multiple uses. The surgical drape 44 could include a power cord that is plugged into a normal outlet in the operating room 10 (e.g., in the floor 22 or in the surgical table 40) to thereby supply power to sources 12 within the surgical drape 44. Further examples are contemplated. In all of the examples above, the sources 12 are supplied power within the operating room 10 via a wired connection to a power source.

In the illustrated example, some of the coils can also be used as booster coils 18 when a wired power source and one of the power consumers 16 are not connected thereto. An example of a location of the booster coils 18 includes within the cart 38. When the coils in the cart 38 are booster coils 18, the cart 38 can be positioned adjacent to sources 12 to supply power to the booster coils 18 to be further transmitted to the receivers 14. For example, the cart 38 can be positioned above the source 12 in the floor 22 or adjacent to the source 12 in the wall 20 of the operating room 10. The cart 38 with the booster coils 18 could also be positioned adjacent to movable objects having sources 12 such as the surgical light 24, the service head 30 or the surgical table 40. The coils in the surgical table 40 can also be used as booster coils 18. Like the cart 38, when the coils in the surgical table 40 are booster coils 18, the surgical table 40 can be positioned adjacent sources 12 to supply power to the booster coils 18 to be further transmitted to the receivers 14 (e.g., the sources 12 in the floor 22, the walls 20 or movable objects such as the service head 30 or the surgical table 40). Likewise, the coils in the drape 44 can be booster coils 18 and can receive energy from any of the sources 12 in the operating room 10 (e.g., those outlined above).

Some of the illustrated coils can also be used as a receiver 14 when one of the power consumers 16 is connected thereto. For example, the surgical table 40, the cart 38 and/or the drape 44 could receive the energy from the sources 12 and/or the booster coils 18 to supply power to power consumers 16 in the surgical table 40, the cart 38 or the drape 44 or connected to the surgical table 40, the cart 38 or the drape 44, respectively. The cart 38 can include power consumers 16 using power supplied thereto by the receiver 14 in the cart 38 and/or the cart 38 could include at least one outlet connected to the receiver 14 for supplying power to a power consumer 17 plugged into the outlet. FIG. 3 illustrates some examples of power consumers 16 supplied power by receivers 14 located in the drape 44 and surgical table 40. One example is a patient inter cavity light 50 for illuminating a surgical cavity of the patient 42, with the cavity light 50 being wired to one of the receivers 12 of the drape 44 or the surgical table 40. For example, the cavity light 50 can be on the drape 44 surrounding the surgical cavity or can be on a retractor 55 within the surgical cavity. In another example as illustrated in FIG. 3, a surgeon 52 in the operating room 10 could be wired to the drape 44 via a drape wire 54 and/or to the surgical table 40 via a table wire 56 for providing power to a power pack 58 worn by the surgeon 52. The power pack 58 can supply power to any item worn by the surgeon 52, for example a headlamp 60. The power pack 58 could directly transmit power to the wearable item or can include a battery for storing power for the wearable item. The drape wire 54 and/or the table wire 56 could also be wired to surgical instruments used by the surgeon 52 (e.g., an image capture device for an endoscope 62, an LED light source 64 within the endoscope 62, power tools, electrocautery tools, etc.). It is contemplated that the drape 44 could include an outlet for plugging surgical instruments or any other item into the drape 44 to be supplied power directly from the receiver 14 or from a battery and/or capacitor in the drape 44 supplied power from the receiver 14.

In the illustrated example, the receivers 14 can be located directly on or in the instruments to be used during a surgical procedure. For example, the retractor 55 having the inter cavity light 50 could have the receiver 14 therein, the endoscope 62 could have the receiver 14 therein, or wearable items worn by the surgeon 52 could be or have receivers 14 (e.g., a belt 70 or a headband 72).

The illustrated receivers 14 supply power to any of the power consumers 16 within the operating room 10. Examples of power consumers 16 outlined above include the inter cavity light 50, the image capture device of the endoscope 62, the LED light source 64 of the endoscope 62, the headlamp 60 or a battery in the power pack 58. However, the power consumers 16 can be any item within the operating room 10 requiring power. Further examples include RF ID chip 90 on any device (e.g., on the endoscope 62 as illustrated in FIG. 3), navigation trackers on devices, and any batteries or capacitors of any device in the operating room 10. The power consumers 16 can directly use the power transmitted thereto without storage of power in a battery or capacitor such that the power consumers 16 must receive energy from the source 12 (either directly or via the booster coil 18) to be energized. Moreover, the power consumers 16 can comprise batteries that are charged and/or capacitors that allow the power consumers 16 to store energy and discharge the energy slowly allowing the power consumers 16 to at least temporarily leave the energized field that is created by the source 12 directly or via the booster coil 18.

The operating room 10 as described herein using the source 12 for transmitting energy wirelessly to the receiver 14 (either directly or via the booster coil 18) for powering the power consumer 16 streamlines use of powered devices in the operating room 10. Use of the wireless energy transmission system described herein eliminates clutter and potentially eliminates cables spanning from the surgical table 40 to a boom or wall 20. The wireless energy transmission system can also prevent cables from running all over the floor 22 of the operating room 10 and less wired connections allow surgeons and others in the operating room to move more freely about the operating room 10.

Several receivers 14 could be located in a single wireless power field created by a single one of the sources 12. In such a situation, it is contemplated that the power supplied to the receivers 14 could be used to communicate with a control system 100 within the wireless power field (e.g., at the source and/or at the receivers 14) to determine use of the power transmitted by the source 12. Such use could limit the amount of power used by the receivers 14 by limiting the amount of power transferred thereto or by preventing power from being transmitted to a particular receiver 14. Such determination of use could be according to a priority system. For example, certain devices are allowed to use power transmitted by the source 12 before other devices such that the power used by the other devices is limited or stopped. Alternatively, the time particular receivers 14 receive power could be partitioned to certain time limits such that a first one of the receivers 14 receives energy for a certain period of time, a second one of the receivers 14 receives energy for a certain period of time, etc. It is contemplated that other schemes could be used to determine which receiver 14 receives energy when multiple receivers are in the wireless power field.

Figure 4:
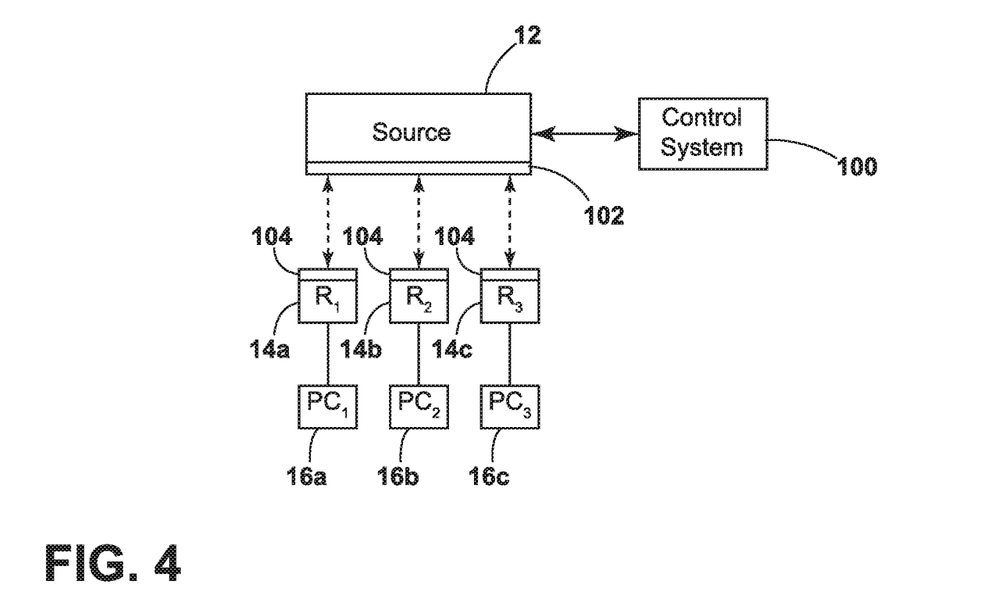
FIG. 4 is a schematic diagram illustrating power arbitration between a source and a plurality of receivers of the present invention.

FIG. 4 illustrates a schematic diagram illustrating power arbitration between the source 12 and a plurality of receivers 14a, 14b, 14c, etc., with each of the receivers 14a, 14b, 14c, etc. being linked to a power consumer 16a, 16b, 16c, etc., respectively. In the illustrated embodiment, the source 12 additionally is or includes an RFID reader/transponder 102. Likewise, each of the receivers 14a, 14b, 14c, etc. additionally is or includes an RFID receiver/transponder 104. The RFID reader/transponder 102 is able to read all of the RFID receiver/transponders 104 of the receivers 14a, 14b, 14c, etc. within the magnetic field thereof to be able to determine the number and/or type of power consumer 16a, 16b, 16c, etc. connected to each of the receivers 14a, 14b, 14c, etc. In FIG. 4, the RFID receiver/transponder 104 includes information related to the power consumer 16a, 16b, 16c, etc., respectively, connected thereto. However, it is contemplated that each of the power consumers 16a, 16b, 16c, etc. could include the RFID receiver/transponder 104 to be read by the RFID reader/transponder 102 of the source 12. In the illustrated example, the RFID reader/transponder 102 relays information related to the number and/or type of power consumer 16a, 16b, 16c, etc. to the control system 100. The control system 100 can then determine which of the power consumers 16a, 16b, 16c, etc. are to receive power before the other power consumers 16a, 16b, 16c, etc. For example, some or all but one of the power consumers 16a, 16b, 16c, etc. can be told to go into standby mode to thereby not consume power (or a very minimal amount of power) until the control system 100 instructs the power consumer 16a, 16b, 16c, etc. to come off of standby mode (via the RFID reader/transponder 102 and the RFID receiver/transponder 104).

Figure 5:
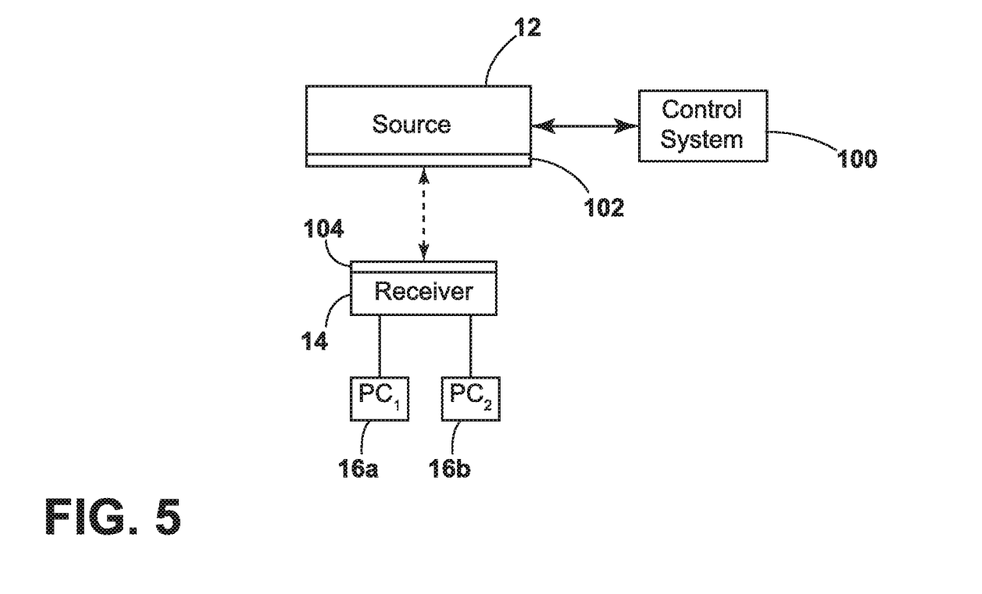
FIG. 5 is a schematic diagram illustrating power arbitration between a source and a plurality of power consumers of the present invention.

In the embodiment of FIG. 5, a single receiver 14 has a plurality of power consumers 16a, 16b, etc. connected thereto. In FIG. 5, the RFID receiver/transponder 104 includes information related to the power consumers 16a, 16b, etc. connected to the receiver 14 thereof. However, it is contemplated that each of the power consumer 16a, 16b, etc. could include the RFID receiver/transponder 104 to be read by the RFID reader/transponder 102 of the source 12. In the illustrated example, the RFID reader/transponder 102 relays information related to the number and/or type of power consumers 16a, 16b, etc. to the control system 100. The control system 100 can then determine which of the power consumers 16a, 16b, etc. are to receive power before the other power consumer 16a, 16b, etc. Once again, it is contemplated that some or all but one of the power consumers 16a, 16b, etc. can be told to go into standby mode to thereby not consume power (or a very minimal amount of power) until the control system 100 instructs the power consumer 16a, 16b, etc. to come off of standby mode (via the RFID reader/transponder 102 and the RFID receiver/transponder 104).

Figure 6:
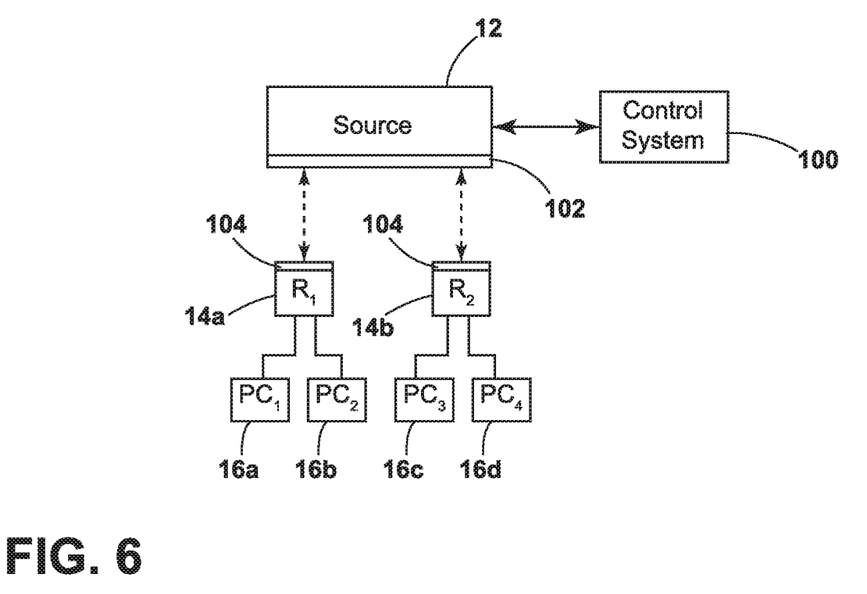
FIG. 6 is a schematic diagram illustrating power arbitration between a source and a plurality of receivers and power consumers of the present invention.

In the embodiment of FIG. 6, a plurality of receivers 14a, 14b, etc. each have a plurality of power consumers 16a, 16b, 16c, 16d, etc. connected thereto. In FIG. 6, each of the RFID receiver/transponders 104 include information related to the power consumers 16a, 16b, 16c, 16d, etc. connected to the receivers 14a, 14b, etc. thereof. However, it is contemplated that each of the power consumers 16a, 16b, 16c, 16d, etc. could include the RFID receiver/transponder 104 to be read by the RFID reader/transponder 102 of the source 12. In the illustrated example, the RFID reader/transponder 102 relays information related to the number and/or type of power consumers 16a, 16b, 16c, 16d, etc. to the control system 100. The control system 100 can then determine which of the power consumers 16a, 16b, 16c, 16d, etc. are to receive power before the other power consumers 16a, 16b, 16c, 16d, etc. Alternatively, the control system 100 can then determine which of the receivers 14a, 14b, etc. are to receive power before the other receivers 14a, 14b, etc. It is contemplated that some or all but one of the power consumers 16a, 16b, 16c, etc. and/or the receivers 14a, 14b, etc. can be told to go into standby mode to thereby not consume and/or receive power, respectively (or a very minimal amount of power) until the control system 100 instructs the power consumers 16a, 16b, 16c, etc. and/or the receivers 14a, 14b, etc. to come off of standby mode (via the RFID reader/transponder 102 and the RFID receiver/transponder 104). While the control system 100 is illustrated as communicating with the source 12, it is contemplated that the control system 100 could directly communicate with the receivers 14a, 14b, etc. and/or the power consumers 16a, 16b, 16c, 16d, etc.

In the embodiments of FIGS. 4-6, while the control system 100 is illustrated as communicating with the source 12, it is contemplated that the control system 100 could directly communicate with the receivers 14a, 14b, 14c, etc. and/or the power consumers 16a, 16b, 16c, etc. Moreover, it is contemplated that the RFID reader/transponder 102 and the RFID receiver/transponder 104 can send and receive information while the source 12 is not sending power and the receivers 14 are not receiving power when the RFID reader/transponder 102 and the RFID receiver/transponder 104 are part of the sources 12 and receivers 14, respectively. Alternatively, if the RFID reader/transponder 102 and the RFID receiver/transponder 104 are separate but connected to the sources 12 and receivers 14, the sources 12 and receivers 14 can run continuously.

Figure 7:
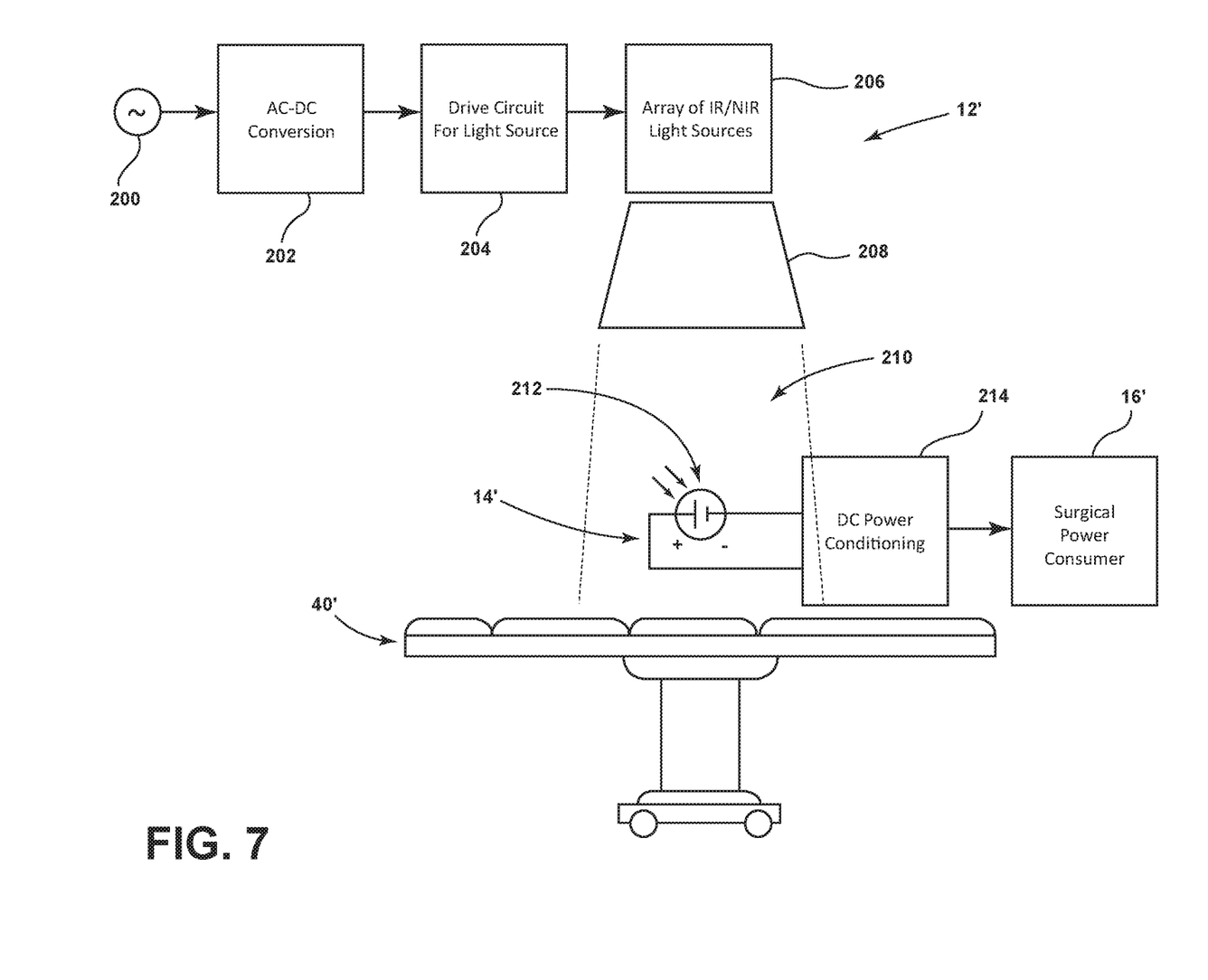
FIG. 7 is a schematic diagram illustrating an embodiment of wireless power transfer of the present invention employing infrared light.

FIG. 7 is a schematic diagram illustrating an embodiment of wireless power transfer of the present invention employing infrared light to transfer power to a power consumer 16'. As illustrated in FIG. 7, power 200 to the surgical room is converted to direct current (DC) in an AC-DC conversion module 202, with the direct current then powering a drive circuit 204 for an infrared light source 206. The infrared light source 206 includes a plurality of infrared lights that emit infrared light. The infrared light source 206 can itself define the source 12' of power or the infrared light source 206 can be integrated with the AC-DC conversion module 202 and/or the drive circuit 204 to define the source 12' of power. It is contemplated that the infrared light source 206 can comprise any element(s) that emit infrared light. For example, the infrared light source 206 can include LEDs and/or lasers. Furthermore, it is contemplated that the infrared light emitted from the infrared light source can be any wavelength of infrared light that can be received by the power receiver 14' to convert the infrared light to power for use by the power consumers 16'. For example, the infrared light can have a near infrared light wavelength of 0.78-3 μm. It is further contemplated that a collimating optical system 208 (e.g., a total internal reflection or lens array) could collimate the light emitted from the infrared light source 206.

In the illustrated example, the power receiver 14' receives the light 210 (e.g., collimated) to convert the infrared light to power for use by the power consumers 16'. The power receiver 14' can include photovoltaic cell 212 that produces DC power. The output of the photovoltaic cell 212 can be outputted to the power consumers 16' or can first be passed through a power conditioning and voltage regulation circuit 214 to produce DC power at a desired voltage before being passed to the power consumer 16'. It is contemplated that the power conditioning and voltage regulation circuit 214 could be integrated into the power consumer 16'.

Figure 8:
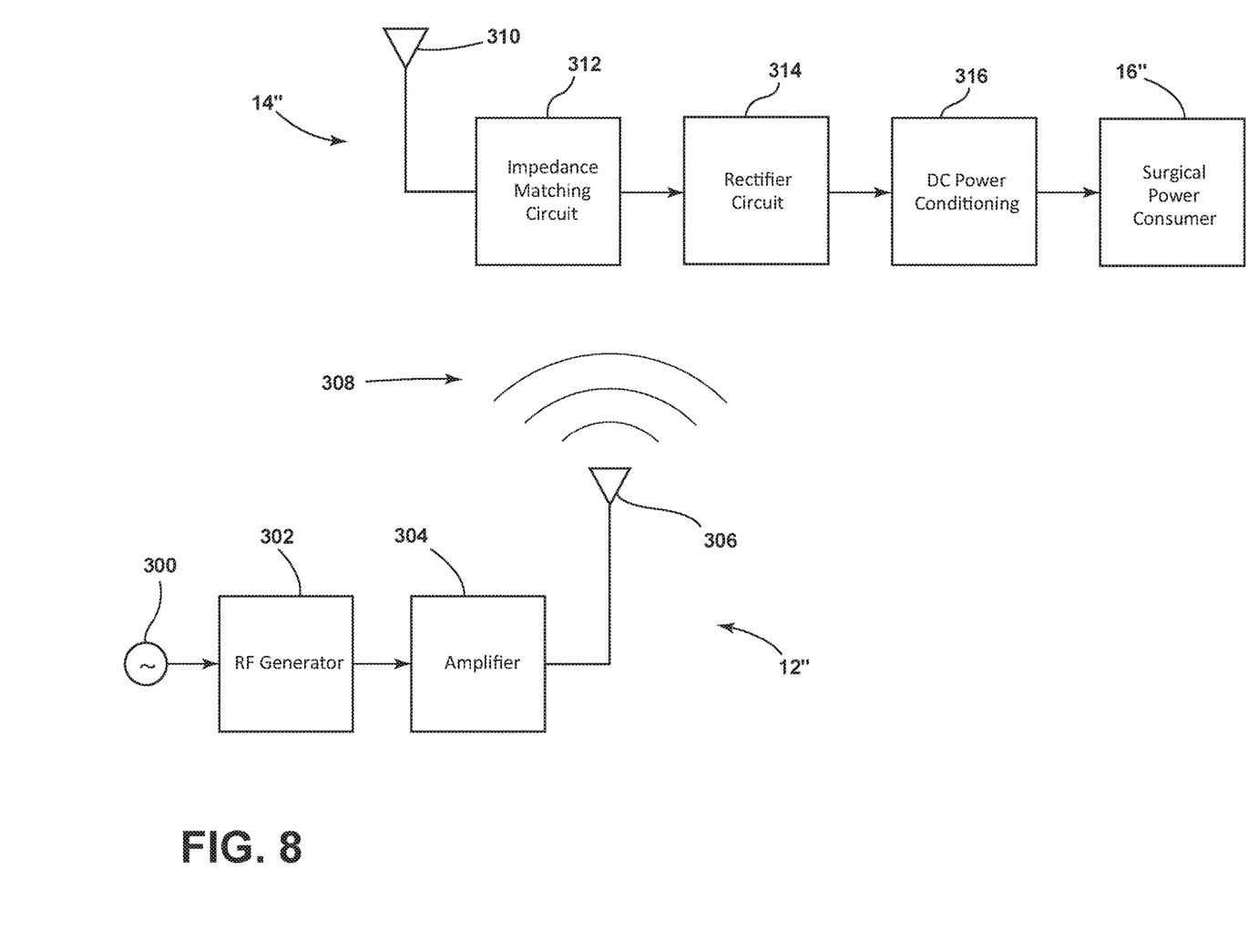
FIG. 8 is a schematic diagram illustrating an embodiment of wireless power transfer of the present invention employing radio frequency energy.

FIG. 8 is a schematic diagram illustrating an embodiment of wireless power transfer of the present invention employing radio frequency energy to transfer power to a power consumer 16'. As illustrated in FIG. 8, power 300 to the surgical room is converted to direct current, with the direct current being employed to generate a radio frequency signal by a radio frequency oscillator 302. It is contemplated that the radio frequency oscillator 302 can generate a radio frequency signal at any usable radio frequency (e.g., 3 KHz to 3 GHz). The radio frequency signal is then amplified in a signal amplifier 304 before being radiated into the environment (e.g., a medical or surgical room) employing a transmission antenna 306, thereby supplying radio signals to the environment that propagate electromagnetic radiation at 308. The RF generator 302 and the antenna 306 can be incorporated into a single device and can define the source 12" or the RF generator 302, the amplifier 304 and the antenna 306 can define the source 12" of power (whether integrated into a single device or using separate devices).

In the illustrated example, the power receiver 14" receives the radio signals to convert the radio signals to power for use by the power consumers 16". The power receiver 14" can include a receiving antenna 310 that can then be fed to an impedance matching circuit 312 that is tuned to resonate at the corresponding frequency of the radio frequency signal, with the radio frequency signal from the impedance matching circuit 312 being rectified in a rectifier circuit 314 to produce a direct current. The direct current can be fed to a direct current power conditioning module 316 to condition and regulate the direct current to a desired voltage for use in the surgical power consumer 16". It is contemplated that the receiving antenna 310, the impedance matching circuit 312, the direct current power conditioning module 316 and/or the power consumer 16" can be integrated into a single unit.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A surgical room power system comprising:
   at least one source of power wired to a power source for the surgical room, the at least one source of power being wired to a surgical room and comprising a source coil;
   at least one power receiver that comprises a receiver coil; and a surgical power consumer wired to the at least one power receiver, the surgical power consumer being configured to assist a surgeon during a surgical procedure on a patient;

wherein the at least one source of power wirelessly transfers power to the at least one power receiver for powering the surgical power consumer, wherein the source coil is movable within the surgical room and is located within a movable surgical light.

2. The surgical room power system of claim 1, wherein: the movable surgical light is connected to a movable boom connected to a structural surface of the surgical room.

3. The surgical room power system of claim 1, further comprising a second source coil that is located within a movable surgical service head connected to a movable boom connected to a structural surface of the surgical room, the movable surgical service head having at least one of a gas outlet and a power outlet on a surface thereof.

4. The surgical room power system of claim 1, wherein: a second source coil is located within a surgical table for supporting the patient during the surgical procedure.

5. The surgical room power system of claim 1, wherein: the receiver coil is located within a drape covering the patient during the surgical procedure.

6. The surgical room power system of claim 1, further including: a booster coil; wherein the at least one source of power wirelessly transfers power to the at least one power receiver via the booster coil, with the booster coil wirelessly receiving power from the at least one source of power and wirelessly transferring the power to the at least one power receiver.

7. The surgical room power system of claim 6, wherein: the booster coil is located on a movable surgical table.

8. The surgical room power system of claim 6, wherein: the booster coil is located on a movable wheeled device.

9. The surgical room power system of claim 6, wherein: the booster coil is located within a drape covering the patient during the surgical procedure.

10. The surgical room power system of claim 1, wherein: the surgical power consumer comprises a patient inter-cavity light for illuminating a surgical cavity of the patient.

11. The surgical room power system of claim 1, wherein: the surgical power consumer comprises a headlamp for the surgeon.

12. The surgical room power system of claim 1, wherein: the surgical power consumer comprises an energy storage device for a surgical device.

13. The surgical room power system of claim 1, wherein: the surgical power consumer comprises an LED.

14. The surgical room power system of claim 1, wherein: the surgical power consumer comprises an RF ID chip of a surgical device.

15. The surgical room power system of claim 1, wherein: the power is transferred using resonant inductive coupling.

16. The surgical room power system of claim 1, wherein: the surgical power consumer comprises an image capture device.

17. The surgical room power system of claim 1, wherein: the power is transferred using radio frequency energy.

18. The surgical room power system of claim 17, wherein: the at least one power receiver is an antenna.

19. The surgical room power system of claim 1, wherein: the power is transferred using infrared light.

20. The surgical room power system of claim 19, wherein: the at least one source of power comprises at least one infrared light emitter; and the at least one power receiver comprises at least one infrared light receiver.

21. A method of supplying power to a surgical power consumer in a surgical room, the method comprising:
providing a surgical patient;
conducting a surgical procedure on the surgical patient;
wiring at least one source of power to a power source for the surgical room, the at least one source of power comprising a source coil that is movable within the surgical room and located within a movable surgical light;
providing at least one power receiver, the at least one power receiver comprising a receiver coil;
wiring the surgical power consumer to the at least one power receiver, the surgical power consumer being configured to assist a surgeon during the surgical procedure on the patient; and
wirelessly transferring power from the at least one source of power to the at least one power receiver for powering the surgical power consumer.

22. The method of supplying power to the surgical power consumer in the surgical room of claim 21, further including: connecting the movable surgical light to a movable boom connected to a structural surface of the surgical room.

23. The method of supplying power to the surgical power consumer in the surgical room of claim 21, further including: locating the receiver coil within a drape covering the patient during the surgical procedure.

24. The method of supplying power to the surgical power consumer in the surgical room of claim 21, further including: providing a booster coil; and wirelessly transferring power from the source coil to the at least one power receiver via the booster coil, with the booster coil wirelessly receiving power from the at least one source of power and wirelessly transferring the power to the at least one power receiver.

25. The method of supplying power to the surgical power consumer in the surgical room of claim 24, further including: locating the booster coil on a movable surgical table.

26. The method of supplying power to the surgical power consumer in the surgical room of claim 24, further including: locating the booster coil on a movable wheeled device.

27. The method of supplying power to the surgical power consumer in the surgical room of claim 24, further including: locating the booster coil within a drape covering the patient during the surgical procedure.

28. The method of supplying power to the surgical power consumer in the surgical room of claim 21, wherein: the surgical power consumer comprises a patient inter cavity light for illuminating a surgical cavity of the patient.

29. The method of supplying power to the surgical power consumer in the surgical room of claim 21, wherein: the surgical power consumer comprises a headlamp for the surgeon.

30. The method of supplying power to the surgical power consumer in the surgical room of claim 21, wherein: the surgical power consumer comprises an energy storage device for a surgical device.

31. The method of supplying power to the surgical power consumer in the surgical room of claim 21, wherein: the surgical power consumer comprises an LED.

32. The method of supplying power to the surgical power consumer in the surgical room of claim 21, wherein: the surgical power consumer comprises an image capture device.

33. The method of supplying power to the surgical power consumer in the surgical room of claim 21, wherein: the surgical power consumer comprises a RF ID chip of a surgical device.

34. The method of supplying power to the surgical power consumer in the surgical room of claim 21, wherein: wirelessly transferring power includes using resonant inductive coupling.

35. The method of supplying power to the surgical power consumer in the surgical room of claim 21, wherein: the power is transferred using radio frequency energy.

36. The method of supplying power to the surgical power consumer in the surgical room of claim 35, wherein: the at least one power receiver is an antenna.

37. The method of supplying power to the surgical power consumer in the surgical room of claim 21, wherein: the power is transferred using infrared light.

38. The method of supplying power to the surgical power consumer in the surgical room of claim 37, wherein: the at least one source of power comprises at least one infrared light emitter; and the at least one power receiver comprises at least one infrared light receiver.

39. A medical room power system comprising:
a source of power wired to a power source for a medical room, the source of power being wired to the medical room and comprising a source coil;
a power receiver that comprises a receiver coil; and
a medical power consumer wired to the power receiver, the medical power consumer being configured to assist a physician during a medical procedure on a patient;
wherein the source of power wirelessly transfers power to the power receiver for powering the medical power consumer,
wherein the source coil is movable within the medical room and is located within a movable medical light.

40. The medical room power system of claim 39, wherein: the power is transferred using resonant inductive coupling.

41. The medical room power system of claim 39, wherein: the power is transferred using radio frequency energy.

42. The medical room power system of claim 39, wherein: the power is transferred using infrared light.

43. The medical room power system of claim 39, wherein: the source of power comprises an infrared light emitter; and the power receiver comprises an infrared light receiver.

* * * * *

UNITED STATES PATENT AND TRADEMARK OFFICE
CERTIFICATE OF CORRECTION

PATENT NO. : 11,121,583 B2
APPLICATION NO. : 16/254749
DATED : September 14, 2021
INVENTOR(S) : Gianni Boccoleri et al.

Page 1 of 1

It is certified that error appears in the above-identified patent and that said Letters Patent is hereby corrected as shown below:

On the Title Page

Item (72), the following inventor information should be added:
--Yousef Hussein QATTAN, Wylie, Texas, United States of America;--

Signed and Sealed this
Ninth Day of July, 2024

Katherine Kelly Vidal
*Director of the United States Patent and Trademark Office*